US010064564B2

(12) United States Patent
Kowalski et al.

(10) Patent No.: US 10,064,564 B2
(45) Date of Patent: Sep. 4, 2018

(54) METHOD OF CMAP MONITORING

(71) Applicant: MEDTRONIC CRYOCATH LP, Toronto (CA)

(72) Inventors: Marcin Kowalski, New York, NY (US); Scott A. Ransom, Marysville, WA (US); Nicolas Coulombe, Anjou (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 467 days.

(21) Appl. No.: 13/974,639

(22) Filed: Aug. 23, 2013

(65) Prior Publication Data
US 2015/0057563 A1 Feb. 26, 2015

(51) Int. Cl.
*A61B 5/04* (2006.01)
*A61B 18/02* (2006.01)
(Continued)

(52) U.S. Cl.
CPC ........ *A61B 5/04001* (2013.01); *A61B 5/0488* (2013.01); *A61B 5/4035* (2013.01);
(Continued)

(58) Field of Classification Search
CPC ... A61B 18/1238; A61B 18/02; A61B 5/0488; A61B 5/05; A61B 5/04001;
(Continued)

(56) References Cited
U.S. PATENT DOCUMENTS
4,289,142 A 9/1981 Kearns
4,776,338 A 10/1988 Lekholm et al.
(Continued)

FOREIGN PATENT DOCUMENTS
CA 2159564 9/1997
EP 0573311 A1 6/1993
(Continued)

OTHER PUBLICATIONS
Andrade, et al. "Cryoballoon ablation for atrial fibrillation." Indian pacing and electrophysiology journal 12.2 (2012): p. 39-53. Retrieved from <http://www.ncbi.nlm.nih.gov/pmc/articles/PMC3337368/pdf/ipej120039-00.pdf> on Mar. 6, 2015.*
(Continued)

*Primary Examiner* — David J McCrosky
(74) *Attorney, Agent, or Firm* — Christopher & Weisberg, P.A.

(57) ABSTRACT

A method and system for monitoring phrenic nerve function and preventing phrenic nerve injury during cardiac ablation. The system includes a pacing device operable to transmit stimulation energy to the phrenic nerve through target tissue proximate the phrenic nerve, a plurality of assessment electrodes operable to make comparisons between baseline, real-time, and predetermined threshold values for CMAP signal amplitude and amplitude over time. The processing device may be connected to an ablation console, and the processing device may interrupt or adjust an ablation procedure controlled by the ablation console and/or generate a system alert in response to one of these comparisons, if the comparison indicates phrenic nerve injury. The method includes applying stimulation energy to the phrenic nerve, recording diaphragmatic CMAP signals in response to the stimulation energy, and adjusting an ablation procedure and/or automatically generating a system alert in response to comparisons performed by the processing device.

17 Claims, 12 Drawing Sheets

(51) Int. Cl.
*A61B 5/0488* (2006.01)
*A61B 5/00* (2006.01)
A61B 18/00 (2006.01)
A61B 17/00 (2006.01)

(52) U.S. Cl.
CPC ............ *A61B 5/4836* (2013.01); *A61B 18/02* (2013.01); *A61B 2017/00044* (2013.01); *A61B 2018/00351* (2013.01); *A61B 2018/00577* (2013.01); *A61B 2018/00642* (2013.01); *A61B 2018/00708* (2013.01); *A61B 2018/00839* (2013.01); *A61B 2018/0212* (2013.01)

(58) Field of Classification Search
CPC ................ A61B 5/4836; A61B 5/4035; A61B 2017/00044; A61B 2018/00708; A61B 2018/00839; A61B 2018/00577; A61B 2018/00642; A61B 2018/0212; A61B 2018/00351; A61N 1/3601; A61N 1/3611
USPC .... 600/529, 534, 536, 546, 554; 606/21, 34; 607/42
See application file for complete search history.

(56) References Cited

U.S. PATENT DOCUMENTS

| | | | |
|---|---|---|---|
| 5,215,082 A | 6/1993 | Kallok et al. | |
| 5,540,732 A | 7/1996 | Testerman | |
| 5,707,398 A | 1/1998 | Lu | |
| 5,758,652 A | 6/1998 | Nikolic | |
| 5,782,826 A | 7/1998 | Swanson | |
| 5,980,463 A | 11/1999 | Brockway et al. | |
| 6,064,910 A | 5/2000 | Andersson et al. | |
| 6,085,118 A | 7/2000 | Hirschberg et al. | |
| 6,126,611 A | 10/2000 | Bourgeois et al. | |
| 6,269,269 B1 | 7/2001 | Ottenhoff et al. | |
| 6,278,894 B1 | 8/2001 | Salo et al. | |
| 6,600,949 B1 | 7/2003 | Turcott | |
| 6,641,542 B2 | 11/2003 | Cho et al. | |
| 6,752,765 B1 | 6/2004 | Jensen et al. | |
| 6,772,008 B2 | 8/2004 | Zhu et al. | |
| 7,025,730 B2 | 4/2006 | Cho et al. | |
| 7,094,207 B1 | 8/2006 | Koh | |
| 7,142,919 B2 | 11/2006 | Hine et al. | |
| 7,160,252 B2 | 1/2007 | Cho et al. | |
| 7,236,828 B2 | 6/2007 | Casavant et al. | |
| 7,245,971 B2 | 7/2007 | Park et al. | |
| 7,299,093 B2 | 11/2007 | Zhu et al. | |
| 7,357,775 B1 | 4/2008 | Koh | |
| 7,371,220 B1 | 5/2008 | Koh et al. | |
| 7,389,140 B1 | 6/2008 | Kroll | |
| 7,392,086 B2 | 6/2008 | Sathaye | |
| 7,647,108 B2 | 1/2010 | Freeberg | |
| 2001/0039419 A1 | 11/2001 | Francischelli et al. | |
| 2004/0122482 A1 | 6/2004 | Tung et al. | |
| 2005/0215990 A1 | 9/2005 | Govari | |
| 2006/0149328 A1 | 7/2006 | Parikh et al. | |
| 2006/0241708 A1 | 10/2006 | Boute | |
| 2007/0027488 A1 | 2/2007 | Kaiser et al. | |
| 2007/0055124 A1 | 3/2007 | Viswanathan et al. | |
| 2007/0118183 A1 | 5/2007 | Gelfand et al. | |
| 2007/0179544 A1 | 8/2007 | Kuehn | |
| 2008/0161657 A1 | 7/2008 | Bullens et al. | |
| 2008/0287820 A1* | 11/2008 | Ignagni et al. ............... | 600/529 |
| 2009/0043352 A1 | 2/2009 | Brooke et al. | |
| 2009/0088827 A1 | 4/2009 | Tockman et al. | |
| 2009/0182318 A1 | 7/2009 | Abboud et al. | |
| 2010/0305637 A1 | 12/2010 | McCabe et al. | |
| 2010/0305638 A1 | 12/2010 | McCabe et al. | |
| 2014/0148725 A1* | 5/2014 | Cadwell ............... | A61B 5/0488 600/546 |

FOREIGN PATENT DOCUMENTS

| | | |
|---|---|---|
| WO | 0038574 A1 | 7/2000 |
| WO | 2004056267 A1 | 7/2004 |
| WO | 2008116232 A1 | 9/2008 |
| WO | 2008144578 A1 | 11/2008 |
| WO | 2009102726 A1 | 8/2009 |

OTHER PUBLICATIONS

Franceschi et al., Diaphragmatic electromyography during cryoballoon ablation: a novel concept in the prevention of phrenic nerve palsy, Heart Rhythm Society, 2011, 7 pages.

Franceschi et al., Phrenic nerve monitoring with diaphragmatic electromyography during cryoballoon ablation for atrial fibrillation: the first human application, Hearth Rhythm, Jan. 2011, 13 pages.

Antz et al., Ablation of Atrial Fibrillation in Humans Using a Balloon-Based Ablation System: Identification of the Site of Phrenic Nerve Damage Using Pacing Maneuvers and CARTO, XP-002629717, May 2006, 4 pages.

Bhagat et al., Capnogrpahy as an aid in localizing the phrenic nerve in brachial plexus surgery. Technical note, Journal of Brachial Plexus and Peripheral Nerve Injury, May 2008, 4 Pages.

Saiful et al., Recordings of Diaphragmatic Electromyograms During Cryoballon Ablation for Atrial Fibrillation can Accurately Predict Phrenic Nerve Palsy, http://www.abstractonline.com/Plan/AbstractPrintView.aspx?mID=2863&sKey=4fb6302., 1 Page.

International Search Report and Written Opinion dated Oct. 20, 2014 for International Application No. PCT/CA2014/000637, International Filing Date: Aug. 22, 2004 consisting of 8 pages.

* cited by examiner

METHOD OF CMAP MONITORING

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and system for monitoring phrenic nerve function and preventing phrenic nerve injury during an ablation procedure.

BACKGROUND OF THE INVENTION

Cryoablation techniques eradicate arrhythmogenic tissue by inducing hypothermia, necrosis, and apoptosis through the application of freezing temperatures to the target cardiac tissue. An unintended consequence of cryoablation, particularly when ablating tissue near the right-sided pulmonary veins in the left atrium, is the attenuation of phrenic nerve function due to the freezing temperatures permeating through the cardiac tissue and into the phrenic nerve. This phenomenon is also a concern when ablating nearby tissue using non-cryogenic ablation modalities, such as radiofrequency ablation. The phrenic nerve is made up mostly of motor nerve fibers that produce contractions of the diaphragm and thus affect breathing and respiration patterns and conditions. In addition, the phrenic nerve provides sensory innervation for many components of the mediastinum and pleura, as well as the upper abdomen, especially the liver, and the gall bladder. Injury to the phrenic nerve may severely impact normal respiratory function and can require many weeks or months to resolve. In the worst cases, this reduced function requires mechanical ventilation assistance to maintain respiration. This side effect of cryoablation can manifest as a transient phrenic functional block, transient phrenic nerve palsy (PNP), or longer-term phrenic nerve injury.

The potential for phrenic nerve injury can be significantly reduced through the use of phrenic nerve monitoring during ablation procedures. By pacing the phrenic nerve superior to the ablation site and monitoring the amplitude of compound motor action potentials (CMAP), the integrity of the phrenic nerve can be continuously assessed during ablation. If cryoablation energy is removed at the first sign of phrenic impairment, the injury is in almost all cases transient, with normal phrenic function returning within minutes.

Currently, phrenic monitoring is typically done using one or more of several possible methods, such as pacing the phrenic nerve and using continuous fluoroscopy during the ablation to visualize a consistent diaphragmatic response, palpitating the abdomen to confirm diaphragmatic movement, intercardiac echocardiography (ICE imaging), or fetal heart monitoring. However, these methods all require vigilance on the part of the operator, and can distract the physician from the main focus of ablating tissue. Additionally, in the case of fluoroscopic monitoring, the patient is exposed to increased x-ray radiation.

It is therefore desirable to provide an automated method of monitoring phrenic nerve function. This automated method would reduce physician distraction, reduce procedure fluoroscopy time, and ensure timely identification of transient injury, leading to prevention of long-term phrenic injury.

SUMMARY OF THE INVENTION

The present invention advantageously provides a system and method for monitoring phrenic nerve function and preventing phrenic nerve injury during an ablation procedure. In one embodiment, the system may generally include a pacing device operable to transmit a stimulation energy to the phrenic nerve through a target tissue proximate the phrenic nerve, a plurality of assessment electrodes operable to detect diaphragmatic compound motor action potential (CMAP) signals in response to the stimulation energy, and a processing device. The processing device may be programmable to determine, based on the CMAP signals detected by the plurality of assessment electrodes, at least one of a baseline amplitude value for the diaphragmatic CMAP signals and a baseline amplitude over time value for the diaphragmatic CMAP signals, the processing device also being programmable to assess in real time at least one of a treatment amplitude value for the diaphragmatic CMAP signals and a treatment amplitude over time value for the diaphragmatic CMAP. Further, the processing device may be programmable to average the diaphragmatic CMAP signals. Still further, the processing device may be programmable to perform several comparisons between signals. For example, the processing device may compare the baseline amplitude value and the treatment amplitude value for the diaphragmatic CMAP signals, compare the treatment amplitude value to a predetermined threshold amplitude value for the diaphragmatic CMAP signals, compare the baseline amplitude over time value and the treatment amplitude over time value for the diaphragmatic CMAP, and compare the treatment amplitude over time value to a predetermined threshold amplitude over time value for the diaphragmatic CMAP. Additionally, the processing device may be programmable to automatically generate a system alert when at least one alert criterion occurs. Alert criteria may include the CMAP signals being out-of-phase between assessment electrodes, the baseline CMAP signal amplitude being low relative to a running average of CMAP signal amplitudes, and stimulation energy failing to be detected by the processing device. The alert criteria may also include the treatment amplitude value exceeding the threshold amplitude value and the treatment amplitude over time value exceeding the threshold amplitude over time value. These alert criteria may indicate phrenic nerve injury. The system may be in communication with a treatment system, such as a treatment system including a console and a treatment device capable of ablating tissue when in use. As a non-limiting example, the treatment system may be a cryoablation system, a radiofrequency ablation system, or combination thereof. Other energy modalities may also be used in the treatment system. The processing device may be programmable to interact with the treatment system to automatically interrupt or adjust the treatment procedure. For example, the processing device may interact with the treatment console, either directly or indirectly (such as when the processing device communicates with a foot switch of the treatment system) to interrupt or adjust the circulation of cryogenic fluid through a treatment element of the treatment device. The processing device may interrupt or adjust the treatment procedure in response to the satisfaction of one or more alert criteria indicating phrenic nerve injury and/or impairment.

In another embodiment, the system may generally include a pacing device operable to transmit stimulation energy to the phrenic nerve through a target tissue structure proximate the phrenic nerve, a plurality of assessment electrodes operable to detect diaphragmatic compound motor action potential (CMAP) signals in response to the stimulation energy, and a processing device programmable to make at least one comparison based on the CMAP signals detected by the plurality of assessment electrodes. The comparison may be, for example, between a baseline amplitude value and a real-time treatment amplitude value for the diaphragmatic CMAP signals, a real-time treatment amplitude value and a predetermined threshold amplitude value for the diaphragmatic CMAP signals, a baseline amplitude over time value and a real-time treatment amplitude over time value for the diaphragmatic CMAP signals, and a real-time treatment amplitude over time value and a predetermined threshold amplitude over time value for the diaphragmatic CMAP signals. The processing device may further be programmable to average the diaphragmatic CMAP signals. The processing device may be in electrical communication with an ablation console, and the ablation console may be in electrical and/or fluid communication with an ablation device. Further, the processing device may be programmable to automatically adjust the operation of the ablation device by the console based on one or more of the comparisons.

A method for monitoring patient phrenic nerve function in response to the transmission of a stimulation energy to the phrenic nerve may generally include applying a stimulation energy from a pacing device to the phrenic nerve, recording diaphragmatic compound motor action potential (CMAP) signals using a plurality of assessment electrodes attached to the patient proximate the xiphoid process and the right costal margin of the patient's ribcage, and transmitting the CMAP signals from the plurality of assessment electrodes to a processing device having a microcontroller. The microcontroller may be programmable to average the CMAP signals, determine a baseline CMAP signal amplitude and a baseline CMAP signal amplitude over time, receive from the plurality of assessment electrodes record real-time CMAP signal amplitudes and CMAP signal amplitudes over time, the real-time CMAP signal amplitudes and amplitudes over time being received during an ablation procedure within the patient's heart, receive from a user a predetermined threshold CMAP signal amplitude value and a predetermined threshold CMAP signal amplitude over time value, compare the baseline CMAP signal amplitude and the real-time CMAP signal amplitudes, compare the baseline CMAP signal amplitude over time and the real-time CMAP signal amplitudes over time, compare the real-time CMAP signal amplitudes and the predetermined threshold CMAP signal amplitude, and compare the real-time CMAP signal amplitudes over time and the predetermined threshold CMAP signal amplitudes over time. Finally, the processing device may be in electrical communication with a cryoablation console having an ablation device positioned in contact with an area of tissue within the patient's heart. The processing device may automatically adjust the amount of heat removed from the area of tissue by the ablation device (for example, interrupting or adjusting the amount of cryogenic fluid circulated within the ablation device and thereby interrupting the ablation of tissue) in response to the comparisons performed by the microcontroller.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
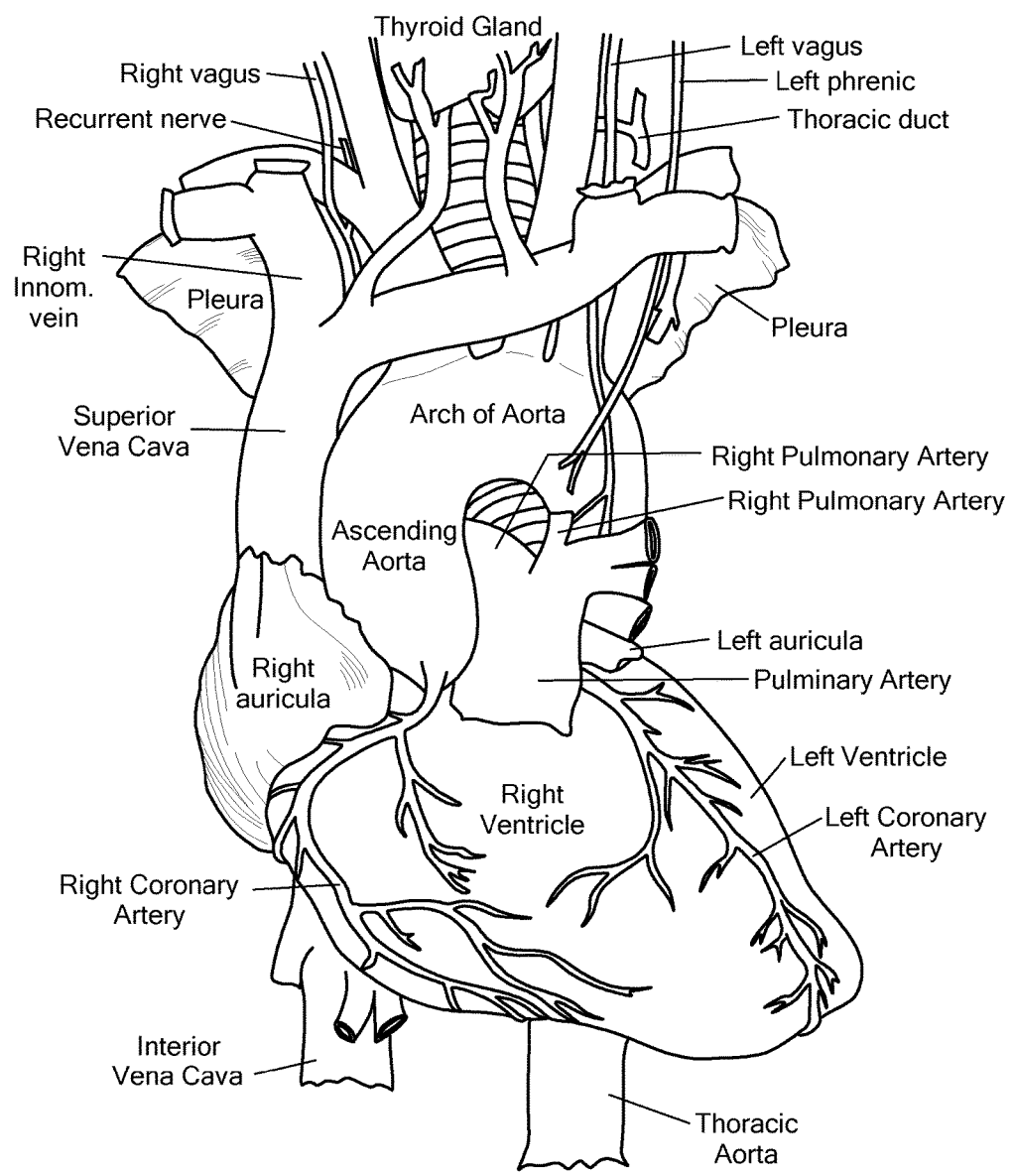
FIG. 1 shows an illustration of a human heart and related anatomy.
Figure 2:
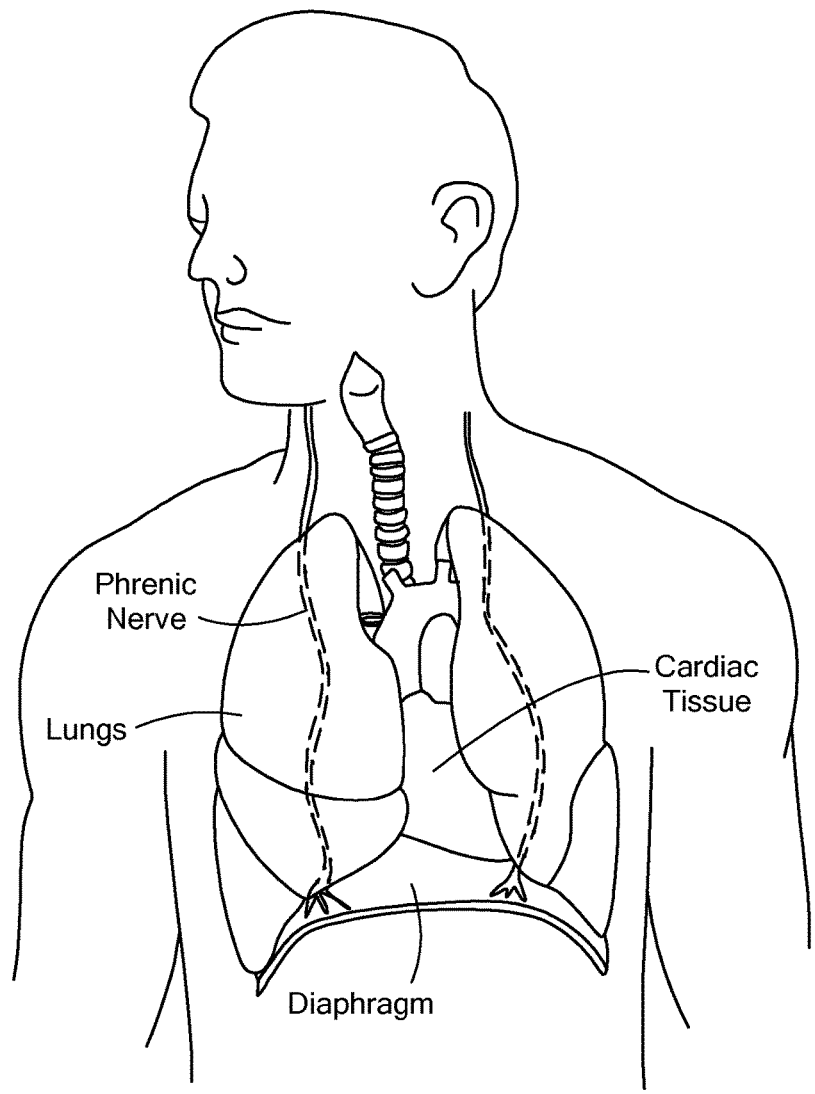
FIG. 2 shows an additional illustration of a human heart and related anatomy.

Referring to FIGS. 1 and 2, the close proximity of the phrenic nerve segments to the right atrium and left ventricle is illustrated. These cardiac regions may be the location or origin of heart arrhythmias or other physiological maladies and thus targeted for tissue ablation in order to remove or otherwise remedy the abnormal electrophysiological occurrence. In thermally treating or ablating select cardiac regions, the phrenic nerve may be at risk of being similarly, although unintentionally, ablated. This could severely impact the normal respiratory functioning of the patient. The risk of such unintentional and undesirable destruction or application of cryogenic treatment or thermal energy to this and other cursory structures compels a desire to monitor or otherwise detect potentially-damaging consequences during treatment.

The phrenic nerve generally includes two segments: the right and left phrenic nerves. Both phrenic nerves run from C3, C4 and C5 vertebrae along the anterior scalene muscle deep to the carotid sheath. The right phrenic nerve passes over the brachlocephalic artery, posterior to the subclavian vein, and then crosses the root of the right lung anteriorly and then leaves the thorax by passing through the vena cava hiatus opening in the diaphragm at the level of T8. The right phrenic nerve passes over the right atrium. The left phrenic nerve passes over the pericardium of the left ventricle and pierces the diaphragm separately.

Figure 3:
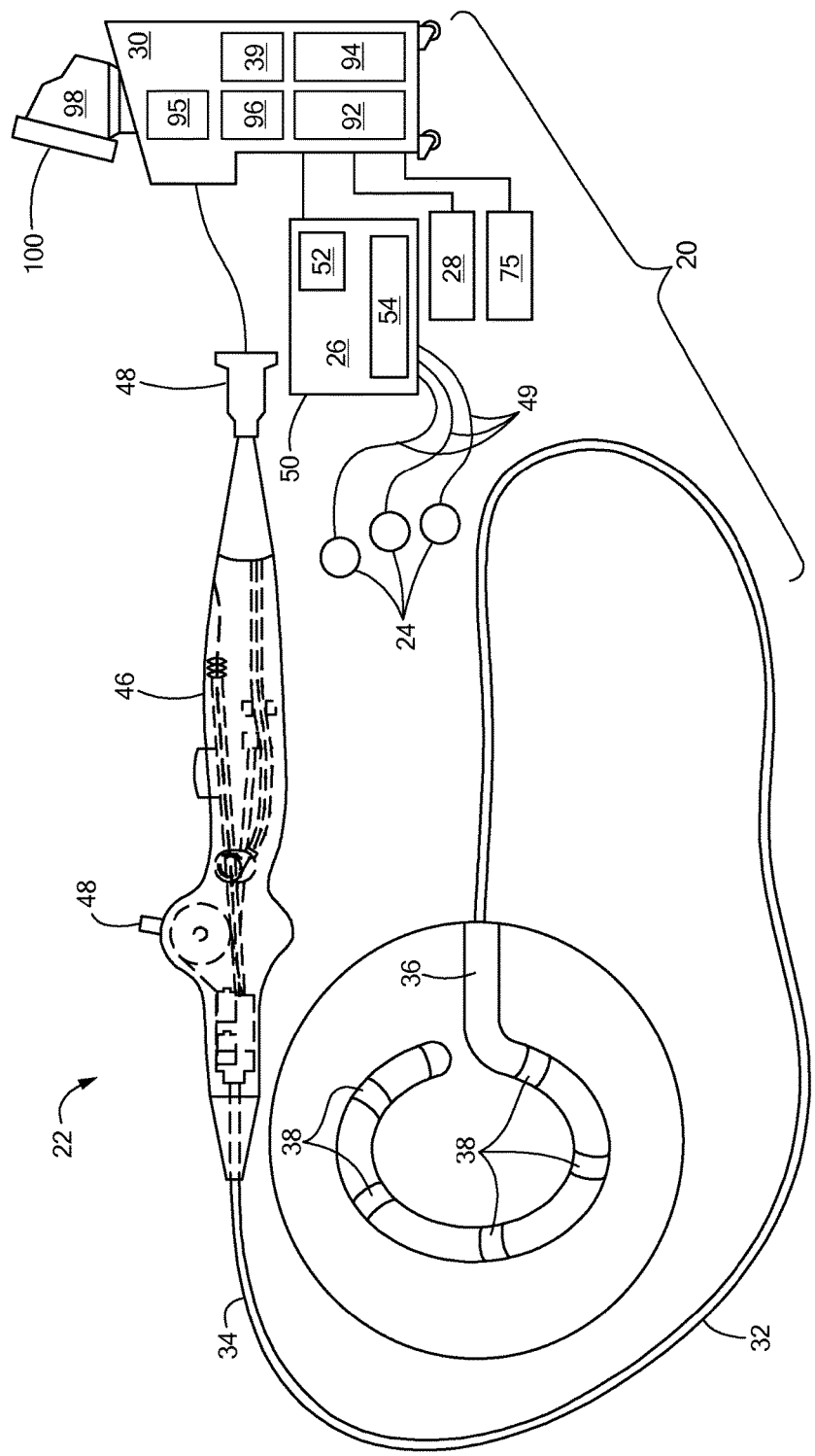
FIG. 3 shows a medical device system constructed in accordance with the principles of the present invention, the medical device system including a pacing device.
Figure 5:
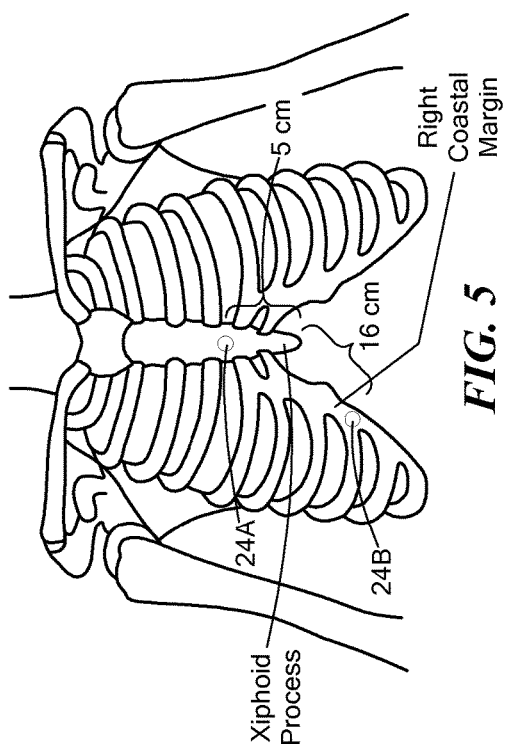
FIG. 5 shows electrode lead positioning on a patient.
Figure 6:
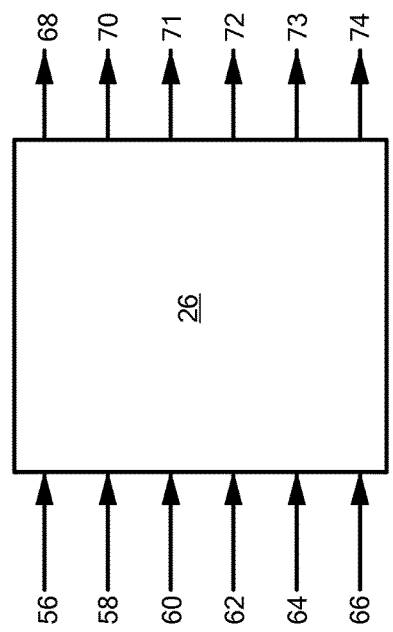
FIG. 6 shows a schematic diagram of the input and output ports of an exemplary processing device.
Figure 4:
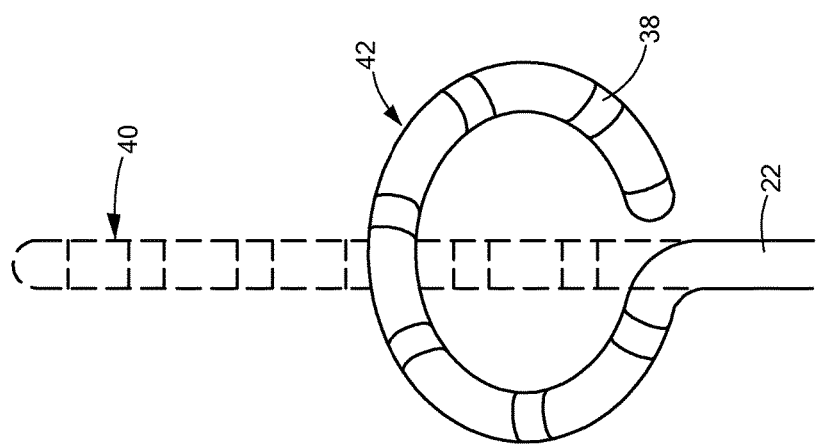
FIG. 4 shows the distal portion of a pacing device.
Figure 7:
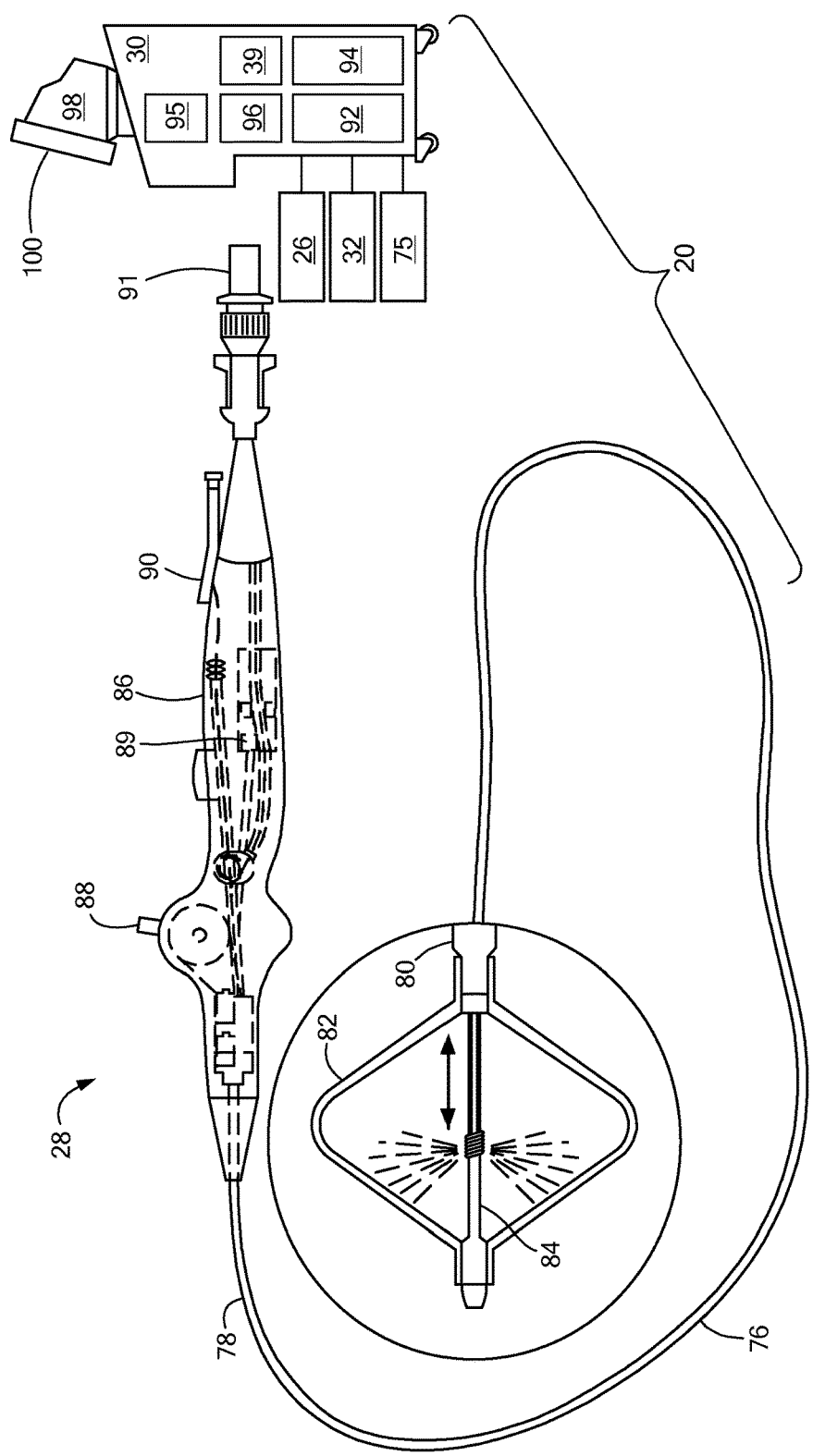
FIG. 7 shows an exemplary treatment device usable with the system of FIG. 4.

Referring now to FIGS. 3-8, a medical device system is shown. The system 20 may generally include a pacing device 22, one or assessment electrodes 24, and a processing device 26 (as shown in FIG. 3). The pacing device 22, assessment electrodes 24, and processing device 26 may be usable with existing treatment systems, such as cryoablation consoles (for example, the CryoConsole Cardiac CryoAblation System (Medtronic, Inc., Minneapolis, Minn.). Thus, existing systems may be retrofitted for assessment functionality, thereby providing the physician with an automated method of monitoring phrenic nerve function during cardiac treatment procedures. The system 20 may be operated in conjunction with a treatment device 28 (as shown in FIG. 7) and a console 30, which may be the same console 30 as shown in FIGS. 3 and 7. The pacing device 22 may include an elongate body 32 sized to be passable through a patient's vasculature. The elongate body 32 may define a proximal portion 34 and a distal portion 36, and may further include one or more lumens disposed within the elongate body 32 to provide mechanical and/or electrical communication between the proximal portion 34 of the elongate body 32 and the distal portion 36 of the elongate body 32. The distal portion 36 of the pacing device 22 may further include one or more pacing electrodes 38. The pacing electrodes 38 may be used to apply electrical and/or magnetic impulses to the phrenic nerve, such indirectly through adjacent tissue like the SVC. As a non-limiting example, the pacing electrodes 38 may be band electrodes that at least partially encircle the device (as shown in FIGS. 3 and 4). However, it will be understood that any size, number, and configuration of pacing electrodes 38 may be used to effectively pace the phrenic nerve. The excitation (i.e. pacing) energy source 39 may be housed within or otherwise provided as part of the console 30, with the pacing device 22 being releasably coupled to the console 30 during operation thereof.

The pacing device 22 may be steerable, or at least transitionable from a substantially linear configuration 40 to an arcuate configuration 42, such as the lasso-type shape shown in FIG. 4. That is, the distal portion 36 of the elongate body 32 may be flexible enough to be deflected in any of a variety of directions and into a circular or semi-circular shape of the lasso-configuration 42. The pacing device 22 may be coupled to an energy source for stimulating tissue. For example, the energy source may be integrated within the processing device 26. The pacing device 22 may include a handle element 46 coupled to the proximal portion 34 of the elongate body 32, where the handle 46 may include an element such as a lever or knob 47 for manipulating the elongate body 32 of the pacing device 22, for example, to transition the distal portion 36 of the elongate body 32 from a substantially linear configuration 40 to a lasso-type configuration 42, or to steer the pacing device 22 through the patient's vasculature to the treatment site. The handle 46 may include an electrical connector 48 for connecting the pacing device 22 to the console 30.

Figure 10:
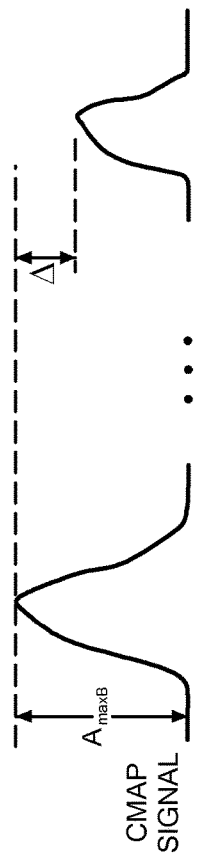
FIG. 10 shows exemplary CMAP signal indicating phrenic nerve injury.

Continuing to refer to FIGS. 3-8, the system 20 may include one or more assessment electrodes 24 in electrical communication with a processing device 26. As a non-limiting example, the system 20 may include a standard set of ten electrodes, signals from which the processing device 26 may use to generate typical 12-lead electrocardiogram (EKG) signal interpretation results. Alternatively, only two or three assessment electrodes 24 may be used (as shown in FIG. 3). The assessment electrodes 24 may be operable to detect compound motor action potential (CMAP), which represents a summation of substantially simultaneous action potentials from several muscle fibers in the same anatomical area. For example, the assessment electrodes 24 may be operable to detect CMAP signals from the diaphragm. Each of the assessment electrodes 24 may be connected to the processing device 26 by a lead 49. The processing device 26 may generally include a housing 50, at least one microcontroller 52, a display 54, one or more user control devices (such as buttons, knobs, and the like), input ports, and output ports (for example, as shown in FIG. 6). It will be understood that as used herein to refer to processing steps, the term "processing device 26" includes the microcontroller 52 and any additional circuitry necessary to perform one or more algorithms required by the processing step. In the non-limiting example shown in FIG. 6, the processing device 26 may include a plurality of input and output ports, including USB ports, serial ports, and user input devices. As shown in FIG. 10, the processing device 26 may include such input ports as a power input port 56, ECG lead input ports 58, an on/off button 60, and user input buttons such as threshold percentage set 62, monitor activation 64, and reset 66. Additionally, the processing device 26 may include such output ports as audio alerts 68 (for example, a connection for a piezoelectric buzzer), visual alerts 70 (for example, one or more LED lights), low amp alerts 71, an output port 72 for a visual display (for example, a parallel or HDMI port connectable to a computer screen), an output port 73 for connection between the processing device 26 and a console 30 (for example, a cryoconsole), and an output port 74 for exporting and storing data, such as a USB or serial port.

The processing device 26 may be in electrical communication with the console 30. For example, when the assessment electrodes 24 transmit signals to the processing device 26 that the processing device 26 interprets as indicating impaired phrenic nerve function or phrenic nerve injury, the processing device 26 may automatically adjust operation of the console 30, such as increasing the temperature of a cryoballoon, stopping the application of radiofrequency energy by the treatment device, or the like. Output port 73 may transmit signals to the console 30 to directly or indirectly adjust treatment characteristics, such as the temperature of the treatment element, phase of ablation energy, pulsing sequence of ablation energy, or the like. The console 30 may include a foot switch 75, and the processing device 26 may communicate with the console 30 to open or close the foot switch in order to stop, start, or otherwise control the administration of ablation energy. In the case of cryoablation using a cryogenic fluid, the processing device 26 may communicate with the console 30 to operate the foot switch 75 to control the flow of cryogenic fluid within, and thus the temperature of, the treatment element. Alternatively, the processing device 26 may be in direct communication with the foot switch 75. It will be understood that the processing device 26 may include additional or different input and output ports than those shown and described herein.

Referring to FIG. 7, the system 20 may be used in conjunction with a treatment device 28 having an elongate body 76 with a proximal portion 78 and a distal portion 80, and a treatment element 82 at the distal portion 80. For example, the treatment element 82 may be a cryoballoon (as shown in FIG. 7. Although not shown, the elongate body 76 may include one or more lumens within the elongate body 76. For example, if the treatment device 28 is configured for use with cryotreatment procedures, the elongate body 76 may include a fluid injection lumen and a fluid exhaust lumen. Additionally, the elongate body 76 may include a guidewire lumen 84 that may be movably disposed within and/or extending along at least a portion of the length of the elongate body 76 for over-the-wire applications. The guidewire lumen 84 may define a proximal end and a distal end, and the guidewire lumen 16 may be movably disposed within the elongate body 76 such that the distal end of the guidewire lumen 84 extends beyond and out of the distal portion of the elongate body 12. Further, the cryoballoon 82 may be affixed to the distal portion of the guidewire lumen 84 at one end and affixed to the distal portion 80 of the treatment device elongate body 76, such that longitudinal movement of the guidewire lumen 84 within the treatment device 28 changes the shape of (such as by compressing or extending) the cryoballoon 84. However, it will be understood that the treatment device 28 can have any type or configuration of one or more treatment elements. As an alternative example, the treatment device 28 may be a focal catheter having one or more radiofrequency electrodes, a basket catheter having a plurality of electrodes affixed to a plurality of splines, or may be any other device capable of ablating cardiac tissue, including, for example, by cryoablation, radiofrequency ablation, ultrasound ablation, laser ablation, hot balloon ablation, or combinations thereof.

Like the pacing device 22, the treatment device 28 may include a handle element 86 coupled to the proximal portion of the elongate body 76, where the handle 86 may include an element such as a lever or knob 88 for manipulating the elongate body 76 of the treatment device 28, for example, to extend or retract the guidewire lumen 84 to adjust the shape of the cryoballoon 82 (or to expand or adjust the size, shape, or configuration of a treatment element other than a cryoballoon), or to steer the treatment device 28 through the patient's vasculature to the treatment site. The handle 86 may further include circuitry 89 for identification and/or use in controlling of the treatment device 28 or another component of the system 20 or device used therewith. For example, the handle 86 may include one or more pressure sensors to monitor the fluid pressure within the treatment device 28. Additionally, the handle 86 may be provided with a fitting 90 for receiving a guidewire that may be passed into the guidewire lumen 84.

The handle 86 may also include connectors 91 that are matable directly to the console 30 by way of one or more umbilicals for providing fluid communication between, for example, a cryogenic fluid source 92 and a cryogenic fluid recovery container 94. Additionally or alternatively, the handle 86 may also include connectors that are matable to the console 30 to provide energy to one or more treatment elements. For example, the handle 86 may be connectable to a power generator 95 (such as a radiofrequency generator, ultrasound generator, light source, or the like) that is located within the console or at an external location. The console 30 may also include a vacuum pump 96 to facilitate removal of expanded cryogenic fluid from the treatment element. The console 30 may further include one or more computers 98, displays 100, user input devices, and the like for controlling the system 20, treatment device 28, and the treatment procedure.

Figure 8:
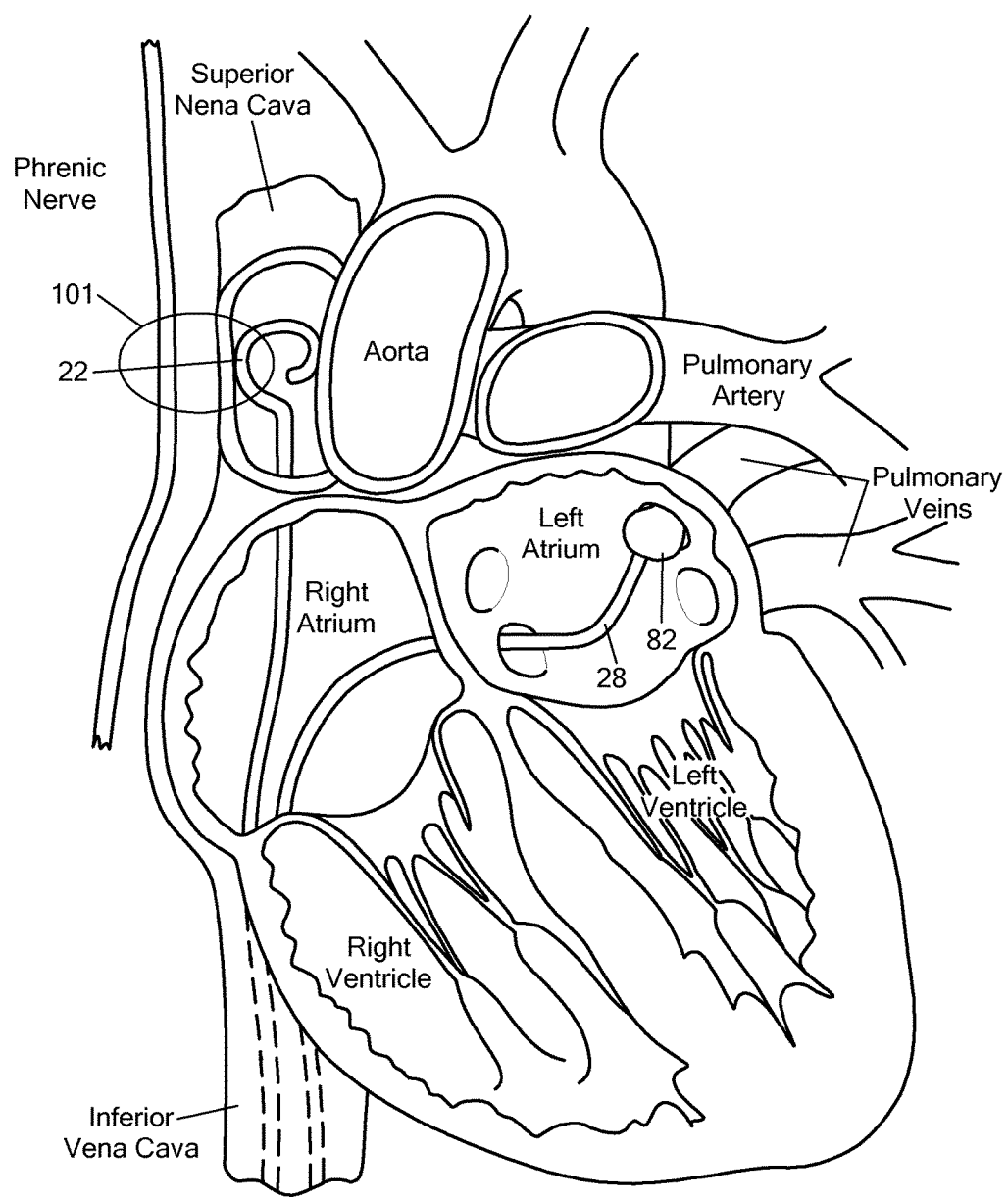
FIG. 8 shows an exemplary placement of a pacing device and a treatment device within a heart.

When the system 20 is in use, each of the assessment electrodes 24 may be attached to an external surface of the patient, such as in the typical 12-lead EKG placement. However, the right arm 24A and left arm 24B electrodes may be placed on the patient as shown in FIG. 5, above the xiphoid process and along the right costal margin to receive CMAP signals which are monitored on lead I during the ablation procedure. Lead I may be the voltage difference between the right arm 24A and left arm 24B electrodes, and thus the positioning shown in FIG. 5 may allow the processing device 26 to monitor signals from the diaphragm. As shown in FIG. 8, for example, the distal portion 36 of the pacing device 22 may be positioned within the superior vena cava (SVC) of the patient's heart and used to transmit electrical impulses to the phrenic nerve through the SVC tissue. The phrenic nerve is within the range of the pacing impulses, shown as area 101. The assessment electrodes 24 then detect and record electrical signals from the diaphragm to monitor phrenic nerve function.

Figure 9:
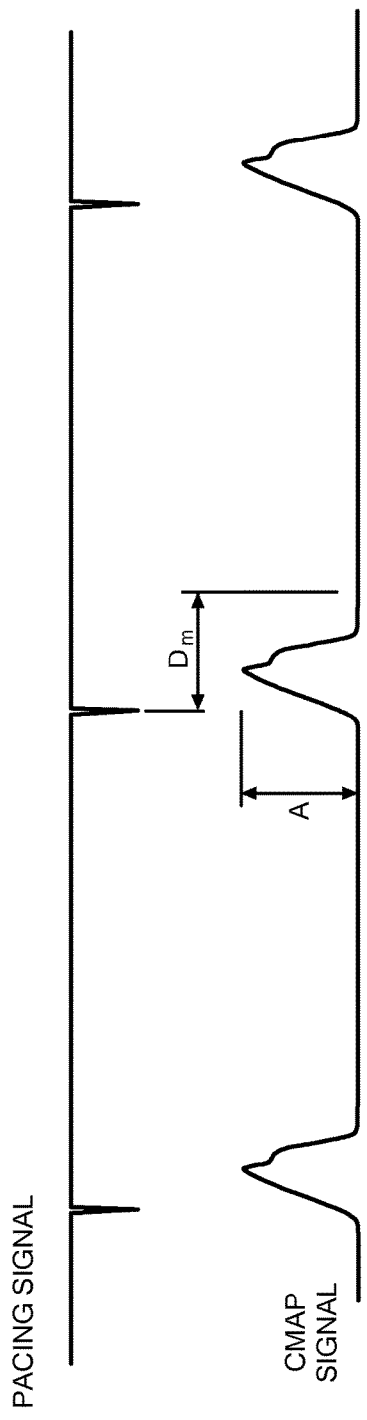
FIG. 9 shows exemplary CMAP signals in response to pacing.

Referring now to FIGS. 9 and 10, exemplary CMAP signals are shown, which may be the type of output generated by the one or more assessment electrodes 24. As shown and described in FIG. 12, the processing device 26 monitors CMAP signal amplitude A during the treatment procedure. FIG. 9 shows CMAP signals in response to pacing, such as by the pacing device 22 positioned within the SVC. $D_m$ is the detection window, the time after the pacing spike during which the processing device 26 may monitor the CMAP signal. FIG. 10 shows a first CMAP signal of which the maximum amplitude ($A_{maxB}$) is determined. The amplitude A of the second CMAP signal is less than $A_{maxB}$ by amount delta Δ. If phrenic nerve impairment occurs as the result of treatment by the treatment device 28, the subsequent CMAP signals may display attenuated amplitude (for example, as shown in the second CMAP signal of FIG. 9). If Δ is greater than the predetermined threshold percentage, the processing device 26 will generate an alert for the operator. The operator may manually enter a desired threshold percentage for an alert to be generated. The threshold may be correlated to Δ; that is, the threshold percentage in CMAP amplitude decline may be set based on a target Δ. For example, the operator may request an alert if the CMAP amplitude is less than approximately 35% of the baseline amplitude.

Figure 11:
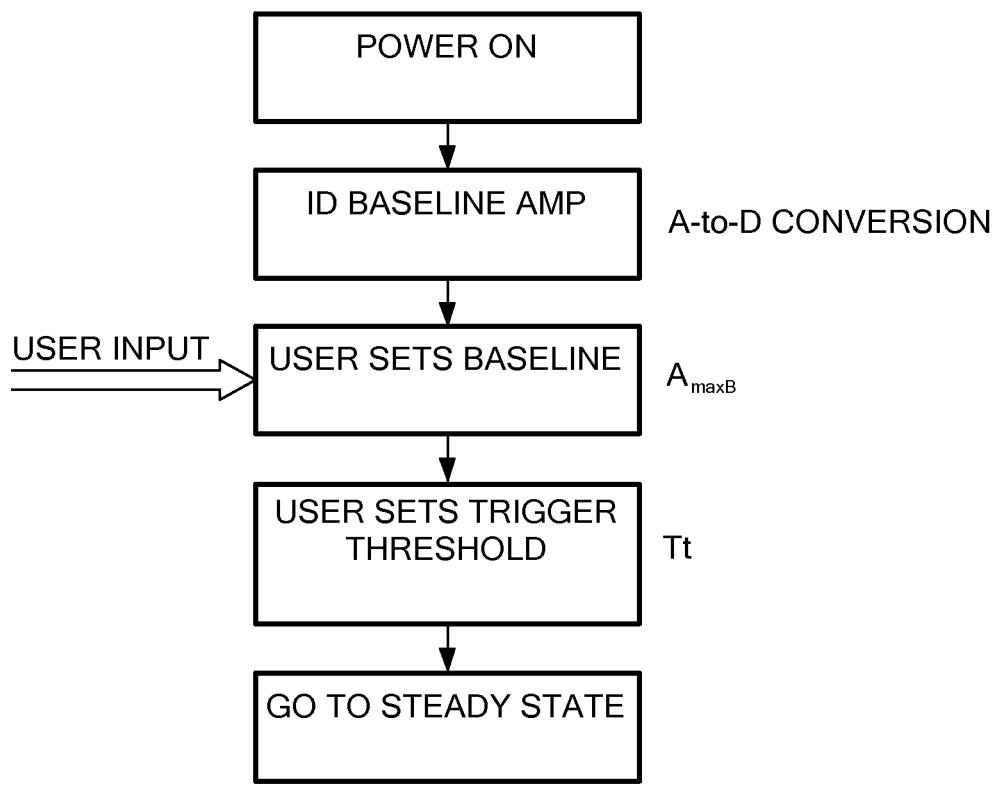
FIG. 11 shows a flowchart of initial processing device operation.
Figure 12:
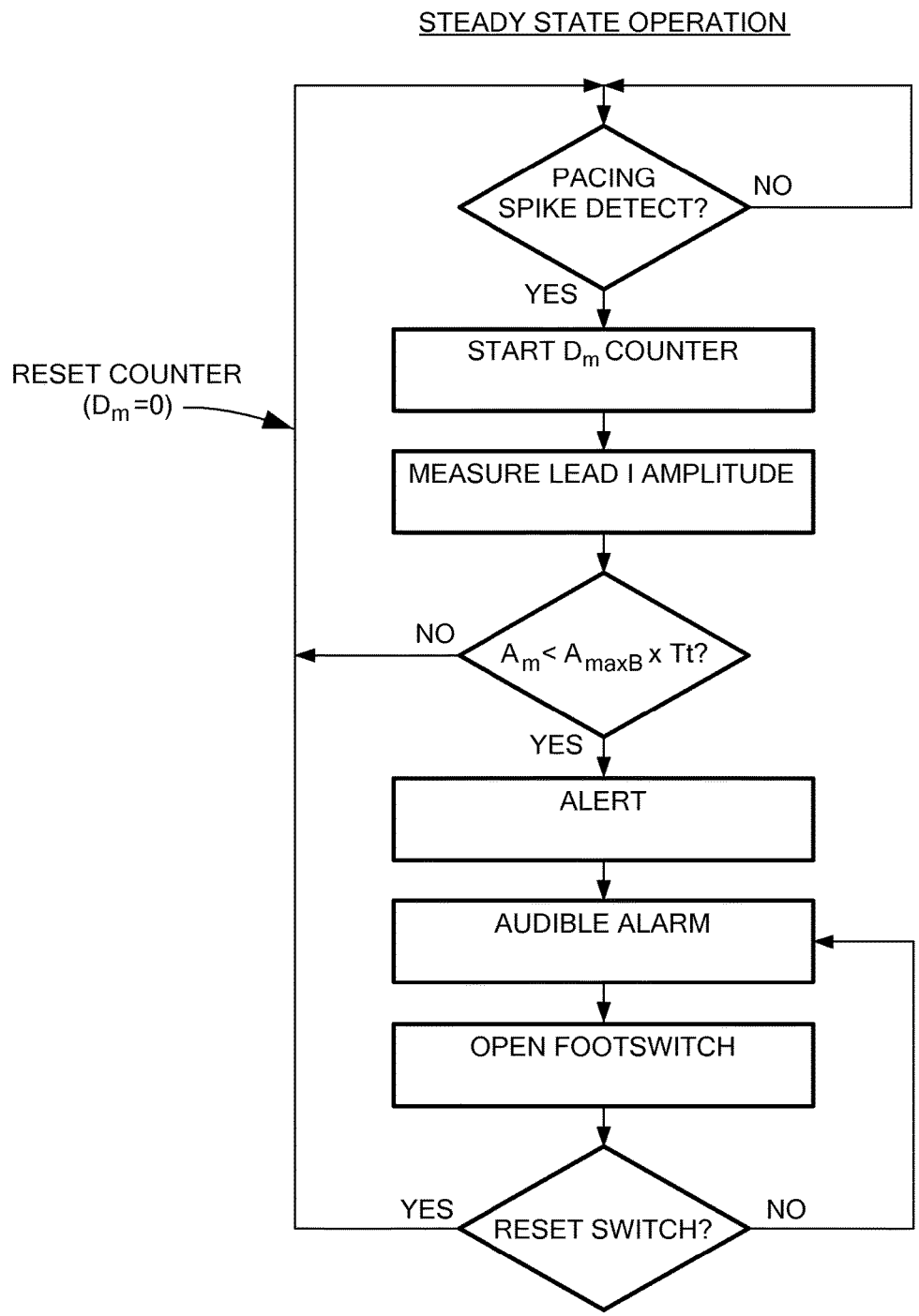
FIG. 12 shows a flowchart of processing device operation in steady state mode.
Figure 13:
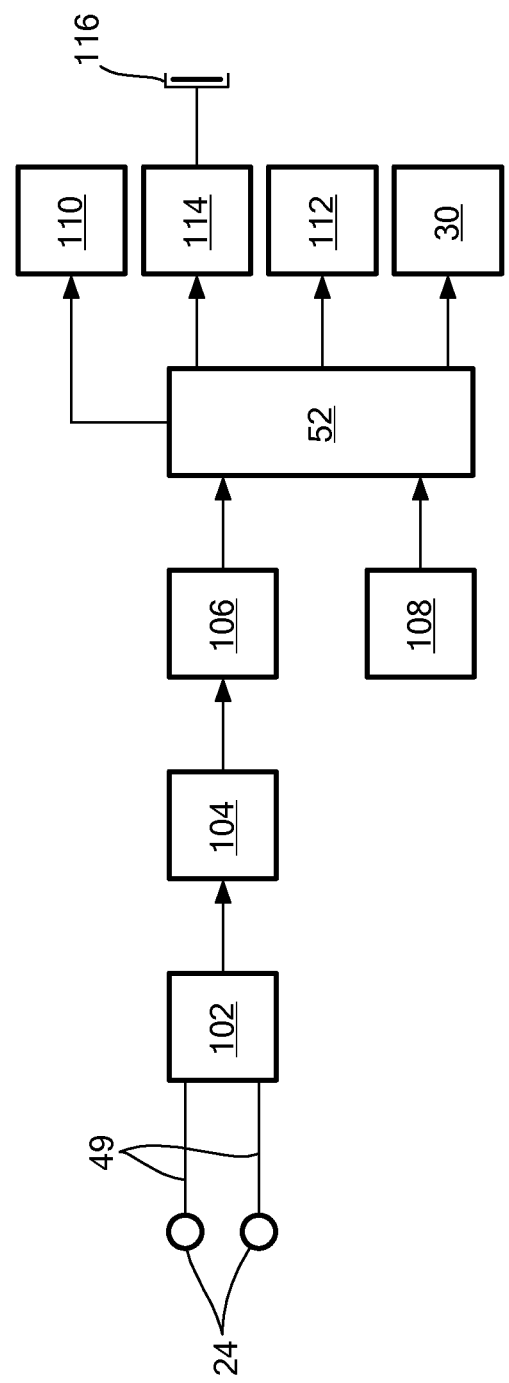
FIG. 13 shows a schematic diagram of signal acquisition, display, and storage.

Referring now to FIGS. 11 and 12, flowcharts of processing device operation are shown. FIG. 11 shows the initial processing device operation, from initialization to steady state mode. As shown, once the physician begins pacing the phrenic nerve using the pacing device 22, the processing device 26 is turned on by the user (although it will be understood that the processing device 26 may be turned on before pacing begins), at which point the processing device 26 identifies the baseline amplitude of CMAP signals obtained from the one or more assessment electrodes 24 affixed to the patient's body and perform a standard analog-to-digital ("A-to-D") conversion on the signals. For example, the processing device 26 may include an algorithm for automatically determining a baseline amplitude value and for identifying substantial variation between heartbeats. For example, a baseline amplitude may be between approximately 1.5 mV and approximately 6 mV. A substantial variation between heartbeats may be indicated if the baseline amplitude changes by more than 0.275 V. The signals may also undergo one or more filtering processes before A-to-D conversion (for example, as shown in FIG. 13). Once a baseline CMAP amplitude is determined, the processing device 26 may generate one or more visual and/or audible alerts that indicate the system 20 is ready for the user to begin ablation. Amplitude data can be stored, exported (for example, using a USB port and device), and/or displayed. If the processing device 26 identifies a low initial amplitude, the processing device 26 may alert the operator that, for example, connections between the processing device 26 and the assessment electrodes 24 and/or between the assessment electrodes 24 and the patient are poor, or that the patient may be more susceptible to phrenic nerve palsy (PNP). The user sets the baseline amplitude ($A_{maxB}$) in the processing device 26. The user then enters into the processing device 26 a threshold percentage of CMAP amplitude decline that will cause the processing device 26 to generate an alert or alarm signal (also referred to as "trigger threshold," $T_t$). In determining this threshold, the user may consider the site of ablation, the duration of treatment, and/or other factors. Further, research suggests that a 30% to 35% reduction in CMAP amplitude during a treatment (i.e. ablation) period is indicative of phrenic nerve impairment. Slope information (i.e. amplitude over time) is also measured. Once these steps are performed, the processing device 26 may be said to be operating in steady state mode.

FIG. 12 shows a flowchart of the processing device operating in steady state mode. Generally, the processing device 26 monitors the amplitude of the CMAP signals received from the assessment electrodes 24 and compares them to the $A_{maxB}$. The processing device 26 also may assess slope information (i.e. amplitude over time). Further, the processing device 26 may include an algorithm that uses pattern and rate analysis to assess complex CMAP waveforms. If the CMAP signal slope and/or amplitude crosses the preset threshold, the processing device 26 identifies this change as impairment of phrenic nerve function and generates and alert signal for the operator and/or communicates with the console 30 to terminate ablation energy to prevent further, and potentially long-lasting, impairment. By alerting the operator to possible phrenic nerve impairment, manifested by a significant measurable decrease in CMAP amplitude during the treatment procedure, the processing device 26 may allow the physician to intervene before phrenic nerve injury occurs, reducing procedural risk and potential patient sequelae.

As shown in the flow chart of FIG. 12, the processing device 26 may first detect the pacing spikes. For example, the device 26 may include a counter with a pacing delay. As a non-limiting example, the pacing delay may be approximately 2500 ms to approximately 3000 ms. If this window of time expires without the processing device 26 detecting any pacing spikes, an indication light may show the user that the processing device 26 has failed to detect any pacing spikes (for example, an LED visible on the processing device 26 may display a red light), and the processing device 26 may emit an audible alert signal. The processing device 26 may then go through a loop and repeat the detection sequence until either pacing spikes are detected or the device 26 is reset. If, on the other hand, the processing device 26 does detect pacing spikes within this window of time, the indication light may display a green light, alerting the user that the pacing spikes have successfully been detected and the remaining steps in the flowchart may be performed. If the processing device 26 is able to detect the pacing spikes, the processing device 26 then starts a counter that records the duration of the measurement cycle, also referred to as the detection window ($D_m$). The counter may be integrated with the microcontroller 52. Next, the processing device 26 may measure the amplitude of the lead I CMAP signals ($A_m$). To do this, the processing device 26 may, for example, employ auxiliary circuitry including an on-board, high-grain instrumentation amplifier with a high common-mode rejection ratio (CMRR) as well as a band-pass filter to detect the signal and reduce extraneous noise artifact. An analog-to-digital circuit can then be used to convert the signal to the digital form used by the device 26 for processing. Next, the processing device 26 may determine whether the amplitude of the lead I CMAP signals ($A_m$) is less than the baseline amplitude ($A_{maxB}$) multiplied by the trigger threshold ($T_t$) ($A_{maxB} \times T_t$ may be referred to as the threshold amplitude value). In other words, the processing device 26 asks the question: $A_m < A_{maxB} \times T_t$? If the answer is no, the counter may reset the measurement cycle duration ($D_m$) to a zero value and start the process from the beginning (i.e. determine whether a pacing spike may be detected). If, on the other hand, the answer is yes, the processing device 26 may generate an alert, for example, an audible alarm, and the processing device 26 may communicate with the console 30 to open (that is, turn off) the foot switch 75. Alternatively, the system 20 may be configured such that the processing device 26 communicates directly with the foot switch 75, and the foot switch communicates to the console 30. In either configuration, the flow of cryogenic fluid, for example, may be reduced or stopped to prevent injury to the phrenic nerve by the treatment device 28. If the foot switch 75 is not reset, the operator alerts may continue and treatment may continue to be stopped or paused. If the foot switch 75 is reset, the processing device 26 may repeat the steady state mode operating cycle by resetting the $D_m$ to a zero value and once again assessing whether pacing spikes are detectible.

Referring now to FIG. 13, a schematic diagram of signal acquisition, display, and storage is shown. The assessment electrodes 24 transmit signals through the leads 49. The signals may then be pre-filtered 102, filtered 104, and may undergo an A-to-D conversion 106. For example, at either the pre-filtering 102 and/or filtering 104 stages, the signals may be averaged to remove the peaks and valleys that may represent noise artifacts. Such filtering may make the signal analysis process less sensitive to sudden shifts and to false positives that may lead to prematurely stopping ablation. The digitalized signals and the operator inputs 108, such as threshold percentage setting, may then enter the microcontroller 52. Data may then be output by the microcontroller 52 to a display 110, to an alert device 112 (for example, one or more LEDs of a visual alert device or a speaker of an audible alert device), to the console 30, or to a data storage device 114. The data storage device 114 may be located within the processing device 26, or the data may be exported from the microcontroller 52 to an external storage device 116, which may be, for example, connected to the processing device 26 via a USB connection.

Figure 14A:
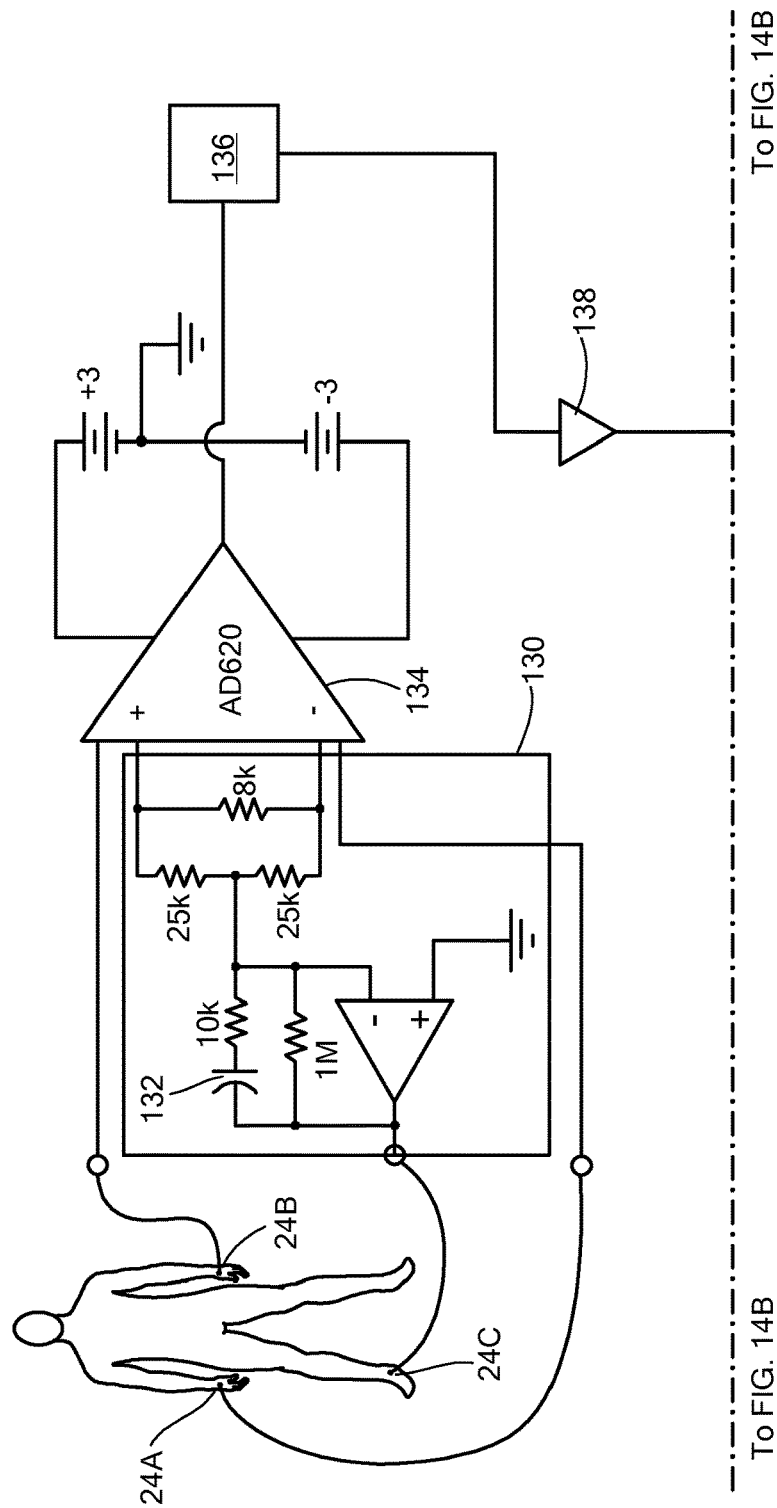
FIGS. 14A and 14B show a circuit diagram of the medical device system.
Figure 14B:
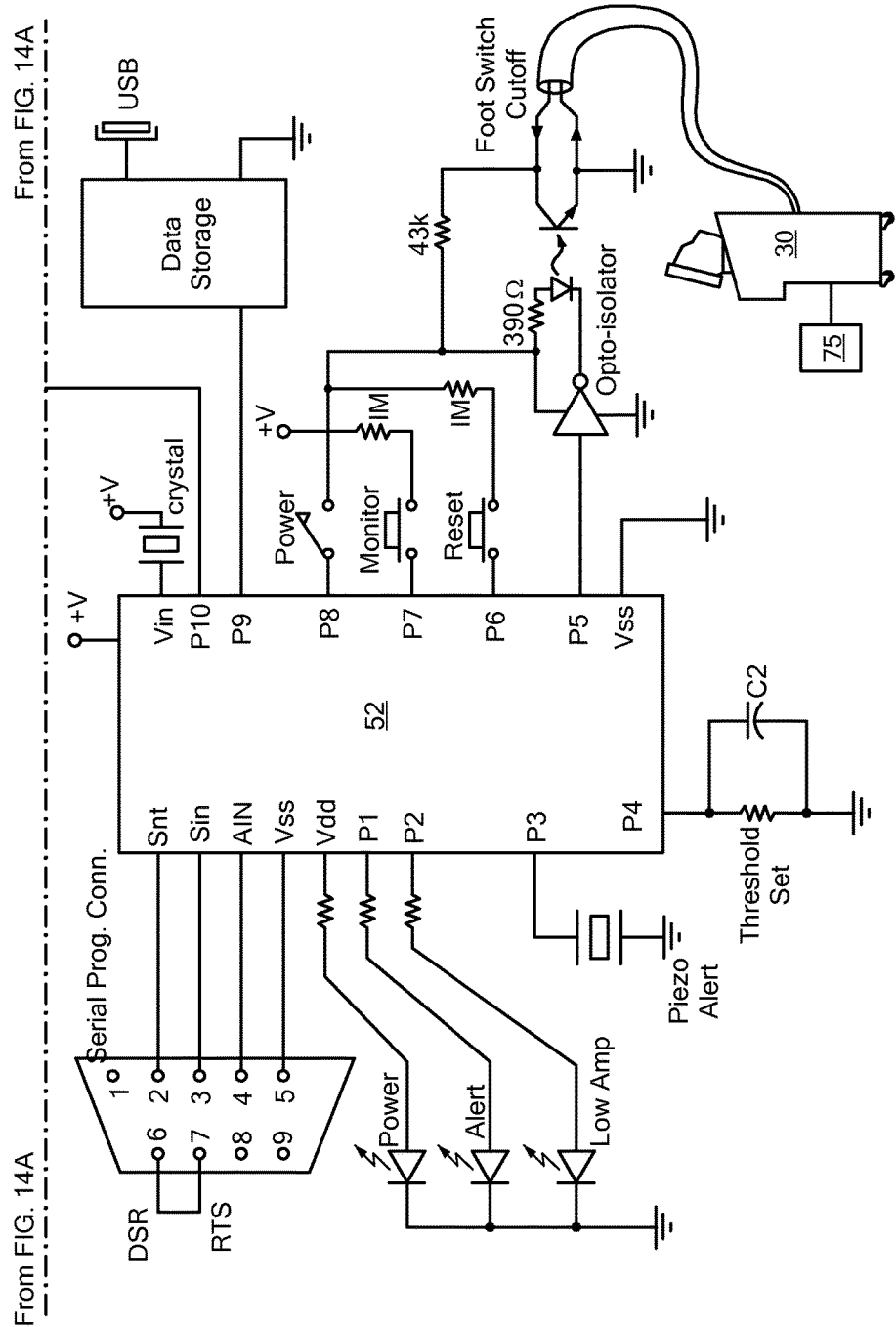

Referring now to FIGS. 14A and 14B, a circuit diagram of the medical device system is shown. For the sake of clarity, the circuit diagram is shown in the separate but connected images of FIGS. 14A and 14B. The circuit may capture the lead I signal, and filtering and gain may be adjusted to optimize CMAP signals. As a non-limiting example, the system 20 may include a parallax stamp microcontroller running a PBASIC interpreter/compiler. The microcontroller 52 may be programmed to run one or more algorithms designed to emulate the operational flow chart shown in FIGS. 11 and 12. The device 26 may use standard ECG acquisition circuitry. Assessment electrodes 24 may be attached to the patient. For example, a right arm 24A electrode and left arm 24B electrode may be used, and an additional right leg electrode 24C. The circuit may include a right-leg drive loop 130 to reduce signal noise, and a capacitor 132 to stabilize the right leg drive loop 130. The circuit may also include an input amplifier 134. The CMAP signals may then undergo filtering, such as by a high-pass filter 136, and the signals may then be amplified by an additional amplifier 138. From the amplifier 138, the signal may then enter the microcontroller 52, at which point the microcontroller 52 may run one or more algorithms to evaluate the signals received and generate an output signal. For example, the microcontroller 52 may assess whether there is a good connection between the assessment electrodes 24 and the patient (that is, the signal is in-range between electrodes 24), whether the CMAP baseline is too low (that is, whether the baseline CMAP amplitude is low relative to a running average; for example, if the CMAP amplitude is less than approximately 1.5 mV), whether pacing spikes are detected, and/or whether the CMAP amplitude is greater or lesser than the threshold baseline ($A_{maxB}$). As shown and described in FIGS. 11-13, the microcontroller 52 may output signals and/or data to one or more alert devices 106, memory devices 108, displays 104, and to the console 30 and/or foot switch 75 to adjust treatment to prevent phrenic nerve injury.

The system 20 automatically monitors phrenic nerve function during ablation of, for example, the right-sided pulmonary veins. By providing a system 20 that automatically detects warning signs for the development of phrenic attenuation or palsy, and that audibly and/or visually alerts the user to these potential issues, patient safety is maximized and physician concerns are alleviated. Further, the system 20 provides an additional level of patient safety when in communication with an ablation console, thereby enabling automatic shut-off if phrenic nerve compromise is detected by the system 20.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system for monitoring phrenic nerve function in response to stimulation energy, the system comprising:
    a stimulation energy source;
    a pacing device including at least one pacing electrode in communication with the stimulation energy source, the at least one pacing electrode being operable to transmit the stimulation energy to the phrenic nerve through a target tissue proximate the phrenic nerve;
    a console including a foot switch and at least one of an energy generator and a cryogenic fluid source in communication with the foot switch;
    a plurality of assessment electrodes operable to detect diaphragmatic compound motor action potential (CMAP) signals in response to the stimulation energy; and
    a processing device including a microcontroller, the microcontroller being in direct communication with the foot switch and programmed to determine, based on the CMAP signals detected by the plurality of assessment electrodes before a delivery of ablation energy, at least one of a baseline amplitude value for the diaphragmatic CMAP signals and a baseline amplitude over time value for the diaphragmatic CMAP signals, the microcontroller also being programmed to:
        (a) assess in real time at least one of a treatment amplitude value for the diaphragmatic CMAP signals and a treatment amplitude over time value for the diaphragmatic CMAP;
        (b) compare the baseline amplitude value for the diaphragmatic CMAP signals and the treatment amplitude value for the diaphragmatic CMAP signals;
        (c) compare the treatment amplitude value for the diaphragmatic CMAP signals to a predetermined threshold amplitude value for the diaphragmatic CMAP signals;
        (d) compare the baseline amplitude over time value for the diaphragmatic CMAP signals and the treatment amplitude over time value for the diaphragmatic CMAP;
        (e) compare the treatment amplitude over time value for the diaphragmatic CMAP signals to a predetermined threshold amplitude over time value for the diaphragmatic CMAP; and
        (f) automatically operate the foot switch in response to at least one of (a)-(e) to at least one of adjust an amount of energy delivered from the energy generator and adjust a flow of cryogenic fluid from the cryogenic fluid source.

2. The system of claim 1, wherein the microcontroller is programmed to average the diaphragmatic CMAP signals.

3. The system of claim 1, wherein the microcontroller is further programmed to automatically generate a system alert when at least one alert criterion occurs, the alert criterion being selected from the group consisting of:
    the CMAP signals are out-of-phase between assessment electrodes;
    the baseline CMAP signal amplitude is low relative to a running average of CMAP signal amplitudes; and
    stimulation energy signals are not detected by the processing device.

4. The system of claim 1, wherein the microcontroller is further programmed to automatically generate a system alert when at least one alert criterion occurs, the alert criterion being selected from the group consisting of:
    the treatment amplitude value is less than the threshold amplitude value; and
    the treatment amplitude over time value is less than the threshold amplitude over time value.

5. The system of claim 4, wherein the microcontroller automatically generates a system alert when the treatment amplitude value is equal to the threshold amplitude value.

6. The system of claim 4, wherein microcontroller automatically generates a system alert when the treatment amplitude value is less than the baseline amplitude by between 30% to 35%.

7. The system of claim 4, wherein the microcontroller automatically generates a system alert when the treatment amplitude over time value is less than the threshold amplitude over time value.

8. The system of claim 1, wherein the system is in communication with a treatment system, the treatment system including the console.

9. The system of claim 8, wherein the treatment system further includes a treatment device coupled to the console, the treatment device having a treatment element operable to reach temperatures sufficient to ablate tissue.

10. The system of claim 9, wherein the treatment element is in communication with the at least one of the energy generator and the cryogenic fluid source in communication with the treatment element.

11. The system of claim 9, wherein the microcontroller is programmed to automatically adjust at least one of the application of ablation energy from the energy generator to the treatment element and the circulation of cryogenic fluid from the cryogenic fluid source through the treatment element in response to at least one alert criterion being met, the at least one criterion being established by the microcontroller.

12. The system of claim 11, wherein the at least one alert criterion is selected from the group consisting of:
    the treatment amplitude value is less than the threshold amplitude value; and
    the treatment amplitude over time value is less than the threshold amplitude over time value.

13. The system of claim 1, wherein the microcontroller is programmable to automatically turn off the foot switch in response to at least one alert criterion being met, the at least one alert criterion being established by the microcontroller.

14. The system of claim 13, wherein the at least one alert criterion is selected from the group consisting of:

the treatment amplitude value is less than the threshold amplitude value; and the treatment amplitude over time value is less than the threshold amplitude over time value.

15. A system for monitoring phrenic nerve function in response to stimulation energy, the system comprising:
a stimulation energy source;
a pacing device including at least one pacing electrode in communication with the stimulation energy source, the at least one pacing electrode being operable to transmit stimulation energy to the phrenic nerve through a target tissue structure proximate the phrenic nerve;
a treatment system including:
a console having a foot switch and at least one of an energy generator and a cryogenic fluid source;
a treatment device coupled to the console, the treatment device having a treatment element operable to reach temperatures sufficient to ablate tissue, the at least one of the energy generator and the cryogenic fluid source being in communication with the treatment element;
a plurality of assessment electrodes operable to detect diaphragmatic compound motor action potential (CMAP) signals in response to the stimulation energy; and
a processing device including a microcontroller that is in direct communication with the foot switch, the microcontroller programmed to make comparisons during a delivery of ablation energy and to determine if phrenic nerve function is impaired based on the comparisons, the comparisons being based on the CMAP signals detected by the plurality of assessment electrodes before and during the delivery of ablation energy to a cardiac tissue, the comparisons being:
a comparison between a baseline amplitude value for the diaphragmatic CMAP signals detected before the delivery of ablation energy and a real-time treatment amplitude value for the diaphragmatic CMAP signals detected during the delivery of ablation energy to the cardiac tissue;
a comparison between a real-time treatment amplitude value for the diaphragmatic CMAP signals detected during the delivery of ablation energy to the cardiac tissue and a threshold amplitude value for the diaphragmatic CMAP signals determined before the delivery of ablation energy;
a comparison between a baseline amplitude over time value for the diaphragmatic CMAP signals detected before the delivery of ablation energy and a real-time treatment amplitude over time value for the diaphragmatic CMAP signals detected during the delivery of ablation energy to the cardiac tissue; and
a comparison between a real-time treatment amplitude over time value for the diaphragmatic CMAP signals detected during the delivery of ablation energy to the cardiac tissue and a threshold amplitude over time value for the diaphragmatic CMAP signals determined before the delivery of ablation energy,
the microcontroller being further programmed to automatically operate the foot switch to at least one of adjust an amount of energy delivered from the energy generator and adjust a flow of cryogenic fluid from the cryogenic fluid source when the microcontroller determines that phrenic nerve function is impaired.

16. The system of claim 15, wherein the microcontroller is further programmed to average the diaphragmatic CMAP signals.

17. A method for monitoring patient phrenic nerve function in response to the transmission of a stimulation energy to the phrenic nerve, the method consisting of:
applying a stimulation energy from a pacing device to the phrenic nerve;
recording diaphragmatic compound motor action potential (CMAP) signals using a plurality of assessment electrodes attached to the patient proximate the xiphoid process and the right costal margin of the patient's ribcage;
transmitting the CMAP signals from the plurality of assessment electrodes to a processing device having a microcontroller, the microcontroller being programmed to:
average the CMAP signals;
determine, before performance of an ablation procedure a baseline CMAP signal amplitude and a baseline CMAP signal amplitude over time; and
receive from a user before the ablation procedure a threshold CMAP signal amplitude value and a threshold CMAP signal amplitude over time value;
performing the ablation procedure, the performing the ablation procedure including the processing device controlling a circulation of cryogenic fluid through a treatment element of an ablation device to remove an amount of heat from an area of tissue within the patient's heart;
receiving with the microcontroller during the ablation procedure real-time CMAP signal amplitudes and CMAP signal amplitudes over time from the plurality of assessment electrodes;
during performance of the ablation procedure, making comparisons with the microcontroller, the microcontroller being programmed to:
compare the baseline CMAP signal amplitude and the real-time CMAP signal amplitudes received during the ablation procedure;
compare the baseline CMAP signal amplitude over time and the real-time CMAP signal amplitudes over time received during the ablation procedure;
compare the real-time CMAP signal amplitudes received during the ablation procedure and the predetermined threshold CMAP signal amplitude;
compare the real-time CMAP signal amplitudes over time received during the ablation procedure and the predetermined threshold CMAP signal amplitudes over time; and
determine if phrenic nerve function is impaired based on the comparisons; and
automatically operating a foot switch with the processing device to adjust a flow of cryogenic fluid through the treatment element of the ablation device to modify an amount of heat removed from the area of tissue by the ablation device during performance of the ablation procedure when the microcontroller determines that phrenic nerve function is impaired, the processing device being in direct communication with the foot switch.

* * * * *